United States Patent
Palagi et al.

(10) Patent No.: US 11,284,923 B2
(45) Date of Patent: Mar. 29, 2022

(54) POLYAXIAL SPINE SCREW ROD HOLDER HAVING A SECOND, OFFSET ROD HOLDER

(71) Applicant: Life Spine, Inc., Huntley, IL (US)

(72) Inventors: Gregory Palagi, Geneva, IL (US); Ra'Kerry Rahman, Houston, TX (US); James M. Freid, Leander, TX (US)

(73) Assignee: Life Spine, Inc., Huntley, IL (US)

( * ) Notice: Subject to any disclaimer, the term of this patent is extended or adjusted under 35 U.S.C. 154(b) by 21 days.

(21) Appl. No.: 16/749,926

(22) Filed: Jan. 22, 2020

(65) Prior Publication Data
US 2020/0229848 A1    Jul. 23, 2020

Related U.S. Application Data

(60) Provisional application No. 62/795,269, filed on Jan. 22, 2019.

(51) Int. Cl.
*A61B 17/70* (2006.01)

(52) U.S. Cl.
CPC ...... *A61B 17/7052* (2013.01); *A61B 17/7014* (2013.01); *A61B 17/7032* (2013.01)

(58) Field of Classification Search
CPC .............. A61B 17/49–52; A61B 17/70–7046
See application file for complete search history.

(56) References Cited

U.S. PATENT DOCUMENTS

| | | | | |
|---|---|---|---|---|
| 8,197,515 B2* | 6/2012 | Levy | ................. | A61B 17/7052 606/250 |
| 8,414,616 B2* | 4/2013 | Berrevoets | ........... | A61B 17/809 606/250 |
| 8,414,617 B2* | 4/2013 | Young | ................ | A61B 17/7052 606/252 |
| 8,758,411 B1* | 6/2014 | Rayon | ................ | A61B 17/7004 606/259 |
| 9,517,089 B1* | 12/2016 | Casey | ................ | A61B 17/7041 |
| 9,737,340 B1 | 8/2017 | Seago | | |
| 9,770,269 B1* | 9/2017 | Shoshtaev | .......... | A61B 17/7055 |
| 10,966,761 B2* | 4/2021 | Lee | .................... | A61B 17/7034 |
| 2005/0228378 A1* | 10/2005 | Kalfas | .................. | A61B 17/705 606/252 |
| 2007/0250061 A1* | 10/2007 | Chin | .................. | A61B 17/7005 606/86 A |
| 2012/0221053 A1* | 8/2012 | Copf | .................. | A61B 17/7035 606/251 |

(Continued)

*Primary Examiner* — Eduardo C Robert
*Assistant Examiner* — Steven J Cotroneo
(74) *Attorney, Agent, or Firm* — Foley & Lardner LLP

(57) ABSTRACT

A spine fixation assembly has a polyaxial spine screw rod holder for a first spine rod and a second rod holder for a second spine rod, the second rod holder is linked to the polyaxial spine screw rod holder via a connector, the connector extending radially outward from the polyaxial spine screw rod holder such that the second rod holder is spatially separated from and offset relative to the polyaxial spine screw rod holder. The polyaxial spine screw rod holder defines a first rod seat that holds the first spine rod. The first spine rod has a first longitudinal axis. The second rod holder defines a second rod seat that holds a second spine rod. The second rod has a second longitudinal axis. The second rod holder is oriented relative to the polyaxial spine screw rod holder by the connector at an offset (angle).

10 Claims, 14 Drawing Sheets

(56) References Cited

U.S. PATENT DOCUMENTS

| | | |
|---|---|---|
| 2013/0123854 A1* | 5/2013 | Kondrashov ...... A61B 17/7038 606/264 |
| 2013/0172938 A1 | 7/2013 | Zido et al. |
| 2014/0277146 A1 | 9/2014 | Li et al. |
| 2017/0079690 A1* | 3/2017 | Oberlander ........ A61B 17/7037 |
| 2017/0086895 A1* | 3/2017 | Barra ................. A61B 17/7037 |
| 2017/0095271 A1* | 4/2017 | Faulhaber ............ A61B 17/705 |
| 2018/0049778 A1 | 2/2018 | Lemerovich |
| 2018/0228516 A1* | 8/2018 | Armstrong ......... A61B 17/8665 |
| 2018/0228518 A1* | 8/2018 | Carruth ................ A61B 17/866 |
| 2018/0243009 A1* | 8/2018 | Bobbitt ............. A61B 17/7037 |
| 2018/0280062 A1* | 10/2018 | Lee ...................... A61B 17/705 |
| 2019/0336178 A1* | 11/2019 | Finn ................... A61B 17/7049 |
| 2020/0367944 A1* | 11/2020 | Loftis ................ A61B 17/7041 |

* cited by examiner

POLYAXIAL SPINE SCREW ROD HOLDER HAVING A SECOND, OFFSET ROD HOLDER

CROSS-REFERENCE TO RELATED APPLICATIONS

This U.S. non-provisional patent application claims the benefit of and/or priority under 35 U.S.C. § 119(e) to U.S. provisional patent application Ser. No. 62/795,269 filed Jan. 22, 2019 titled "Polyaxial Spine Screw Rod Holder Having a Second, Offset Rod Holder," the entire contents of which is specifically incorporated herein by reference.

FIELD OF THE INVENTION

The present invention relates to fixation components for the spine and, more particularly, to polyaxial spine screw rod holders.

BACKGROUND OF THE INVENTION

Many people contend with orthopedic issues as a result of age, disease, and trauma, as well as congenital and acquired complications and conditions. While some of these issues can be alleviated without surgery, other issues respond better to surgery. In some cases, surgery may include the insertion of an orthopedic implant. Orthopedic spine assemblies and constructs such as spine plates, bone screw assemblies for spinal rods and other devices (spinal components) have made a profound contribution to the correction of spinal deformities, accidents and other problems in the cervical as well as thoracic, lumbar and sacral spine. These and other spinal devices are typically fixed to vertebrae using vertebral bone screws. Vertebral bone screws are specially designed and manufactured bone screws that are placed into the bone of a vertebra. Vertebral bone screws placed in the vertebra offer superior strength and pull-out resistance as compared to other forms of fixation in spine surgery. The ability to achieve vertebral fixation has allowed surgeons to obtain more secure fixation of the spinal components involved, which permits more powerful correction of spine problems and reported better clinical outcomes.

In addition to other uses, bone screws provide a solid foundation for the attachment of spinal rods. Spine rods are used for the fixation of a plurality of vertebrae for various situations. A spine rod is held relative to the vertebrae by a spine rod bone screw assembly. Various types of spine rod bone screw assemblies are known such as those that allow for inter-operative adjustments in the coronal, transverse and sagittal planes—generally known as polyaxial bone screw spine rod assemblies, polyaxial spine screw holders, or simply polyaxial spine screws. Other names may also be used. Certain spine rod bone screw assemblies allow for various degrees of freedom of attachment of a spine rod thereto from any direction, angle, and height. In all cases, however, the spine rod bone screw assemblies hold a single spine rod and are fixed to a vertebra. The polyaxial spine screw rod holder assembly thus permits a spine rod to be rigidly locked into a variety of positions along with other types of implant components. This allows a surgeon to tailor-make each construct.

Heretofore, each polyaxial spine screw rod holder assembly held only a single spine rod. However, many spine fixation constructs use more than one spine rod. Each spine rod therefore requires a separate polyaxial spine screw rod holder assembly. It would be advantageous to have a spine rod bone screw assembly that can accommodate more than one spine rod. It would be further advantageous if the spine rod bone screw assembly was polyaxial.

Thus, there is a need for a polyaxial spine screw rod holder assembly that can accommodate more than one spine rod. Other needs are evident.

SUMMARY OF THE INVENTION

A polyaxial spine screw rod assembly provides a spine fixation implant that includes a polyaxial spine screw rod holder with a second rod holder that is coupled to the polyaxial spine screw rod holder via a connector, the connector extending radially outwardly from the polyaxial spine screw rod holder such that the second rod holder is spatially separated from and offset relative to the polyaxial spine screw rod holder. The polyaxial spine screw rod holder defines a first rod seat that holds a first spine rod having a first longitudinal axis. The second rod holder defines a second rod seat that holds a second spine rod having a second longitudinal axis.

The second rod holder is oriented relative to the polyaxial spine screw rod holder by the connector at an offset (angle) thereto. In accordance with one definition, the offset is between a perpendicular to the first longitudinal axis of the first spine rod retained in the first rod seat of the polyaxial spine screw rod holder and a parallel to the first longitudinal axis of the first spine rod retained in the first rod seat of the polyaxial spine screw rod holder. Preferably, but not necessarily, the offset is generally forty-five degrees (45°) from the perpendicular to the first longitudinal axis of the first spine rod retained in the first rod seat of the polyaxial spine screw rod holder and the parallel to the first longitudinal axis of the first spine rod retained in the first rod seat of the polyaxial spine screw rod holder. Other definitions are provided in the detailed description.

Preferably, but not necessarily, the first rod seat of the polyaxial spine screw rod holder is defined by first and second rod pockets, and the second rod seat of the second rod holder is defined by third and fourth rod pockets.

In one form, while maintaining the offset, spatial orientation of the second rod holder is static (fixed) relative to the polyaxial spine screw rod holder. In this form, the second rod holder is fixed relative to the connector. Preferably, but not necessarily, orientation of the second rod seat of the second rod holder aligns with the orientation of the first rod seat of the polyaxial spine screw rod holder such that the second longitudinal axis of the second spine rod retained in the second rod seat of the second rod holder aligns with the first longitudinal axis of the first spine rod retained in the first rod seat of the polyaxial spine screw rod holder. Such spinal rod alignment is preferably, but not necessarily, parallel.

In another form, while maintaining the offset, spatial position and orientation of the second rod holder is dynamic (variable) relative to the polyaxial spine screw rod holder. In this form, spatial position and orientation of the second rod holder is adjustable relative to the connector, and thus adjustable relative to the polyaxial spine screw rod holder. Therefore, orientation of the second rod seat of the second rod holder is rotatable relative to the orientation of the first rod seat of the polyaxial spine screw rod holder such that the second longitudinal axis of the second spine rod retained in the second rod seat of the second rod holder is rotationally positionable relative to the first longitudinal axis of the first spine rod retained in the first rod seat of the polyaxial spine screw rod holder, and spatial orientation of the second rod seat of the second rod holder is independently positionable relative to the first rod seat of the polyaxial spine screw rod holder such that the distance between the second spine rod retained in the second rod holder of the second rod holder relative to the first spine rod retained in the first rod seat of the polyaxial spine screw rod holder may be varied.

Features of the static and dynamic versions of the present polyaxial spine rod bone screw assembly may be interchanged as desirable.

BRIEF DESCRIPTION OF THE DRAWING FIGURES

The above mentioned and other features, advantages and objects of this invention, and the manner of attaining them, will become apparent and the invention itself will be better understood by reference to the following description of two forms of the invention taken in conjunction with the accompanying drawings, wherein.

A description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE INVENTION

Figure 4:
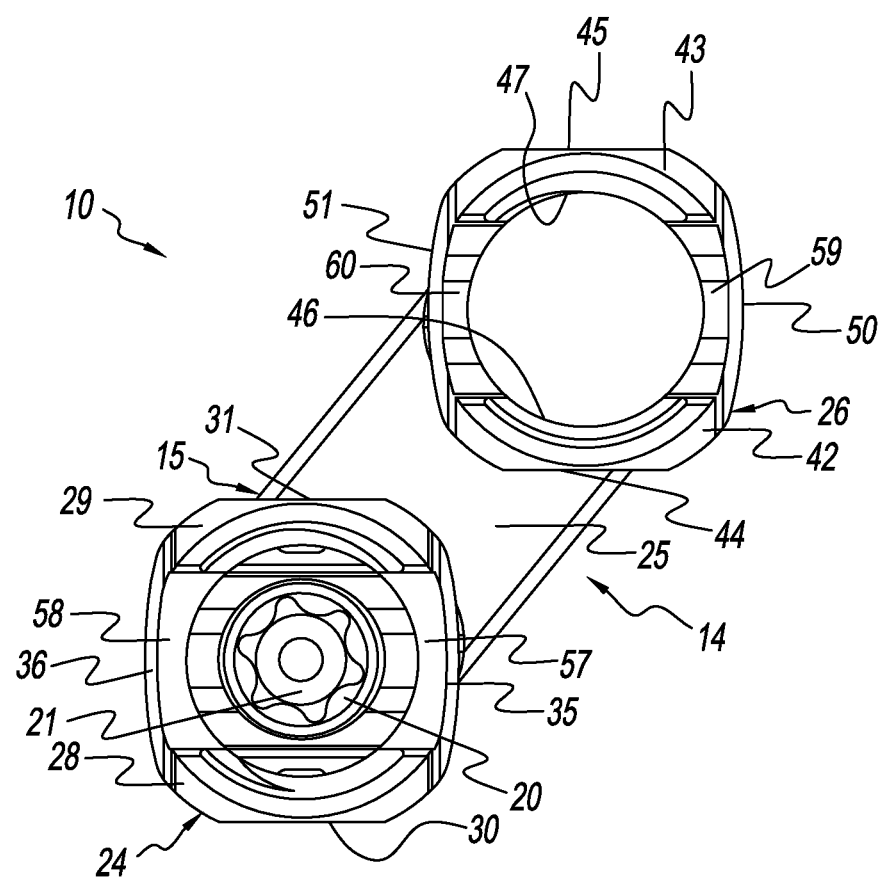
FIG. 4 is a top plan view of another form of a polyaxial spine screw rod holder having a second, offset spine rod holder.
Figure 5:
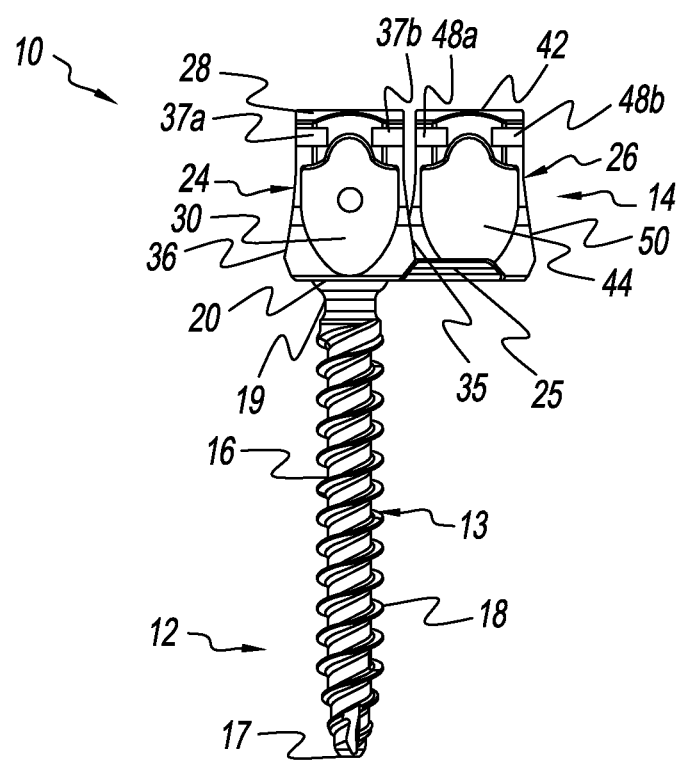
FIG. 5 is a side view of the polyaxial spine screw rod holder having a second, offset spine rod holder of FIG. 4.
Figure 6:
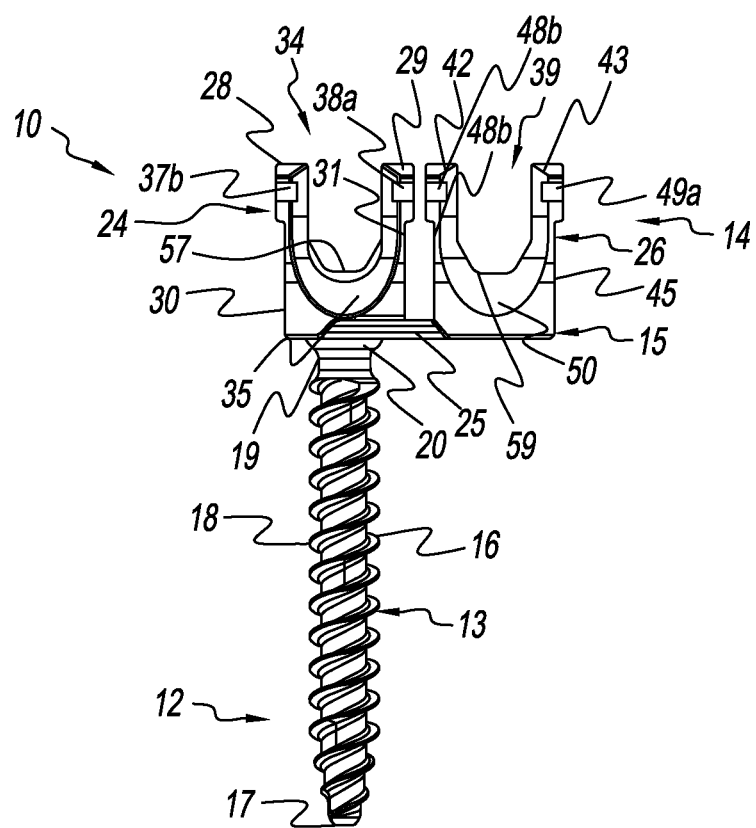
FIG. 6 is another side view of the polyaxial spine screw rod holder having a second, offset spine rod holder of FIG. 4.
Figure 7:
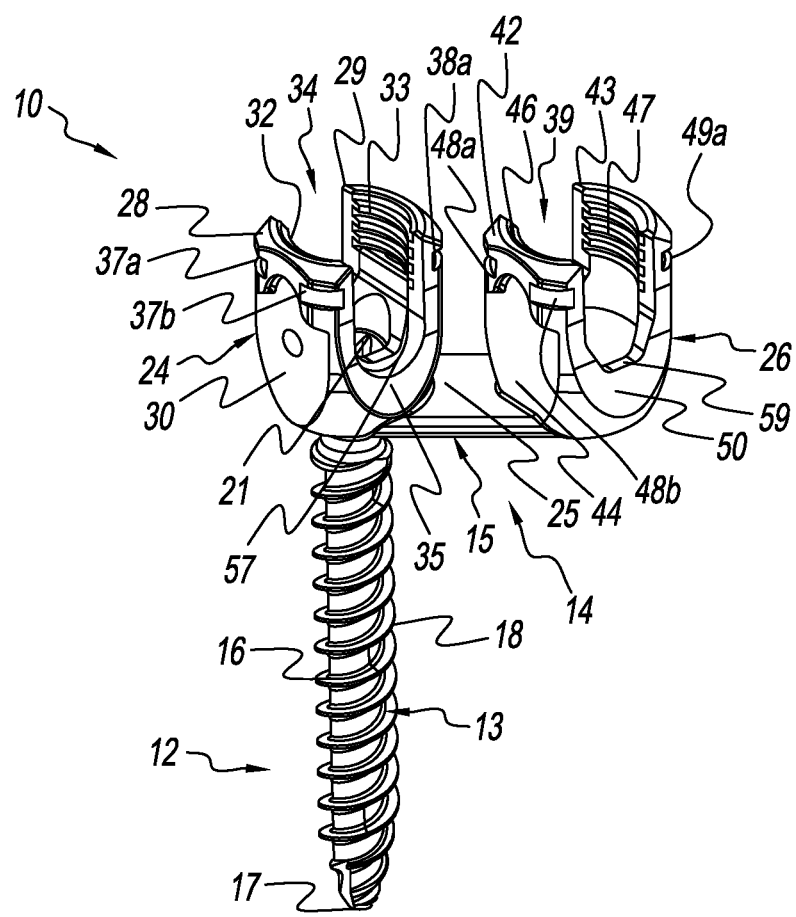
FIG. 7 is a view of the polyaxial spine screw rod holder having a second, offset spine rod holder of FIG. 4.
Figure 8:
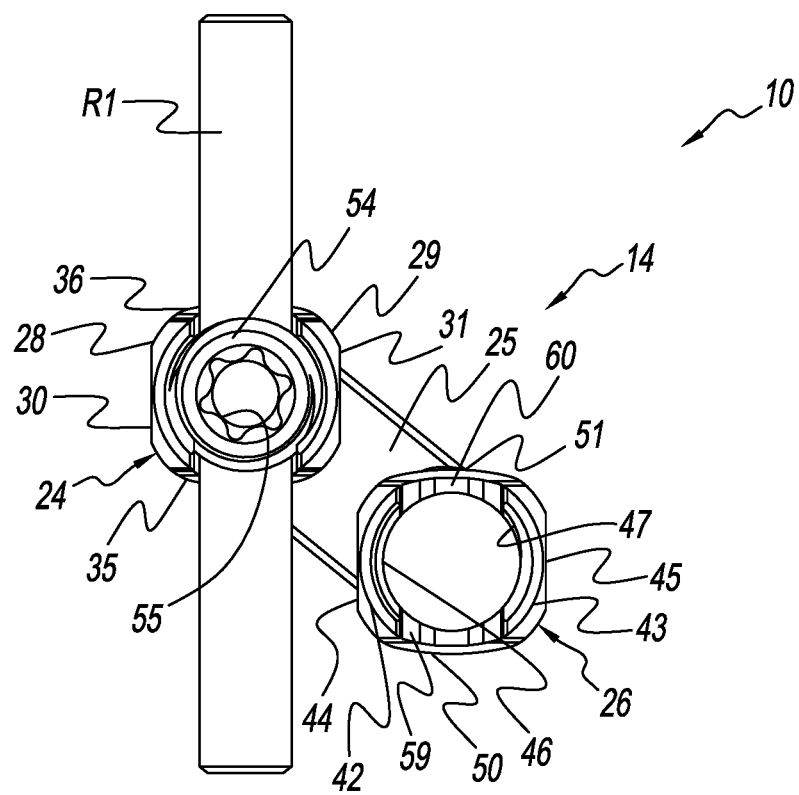
FIG. 8 is a top plan view of the polyaxial spine screw rod holder having a second, offset spine rod holder of FIG. 4 showing a spine rod retained in the polyaxial spine rod holder thereof.
Figure 9:
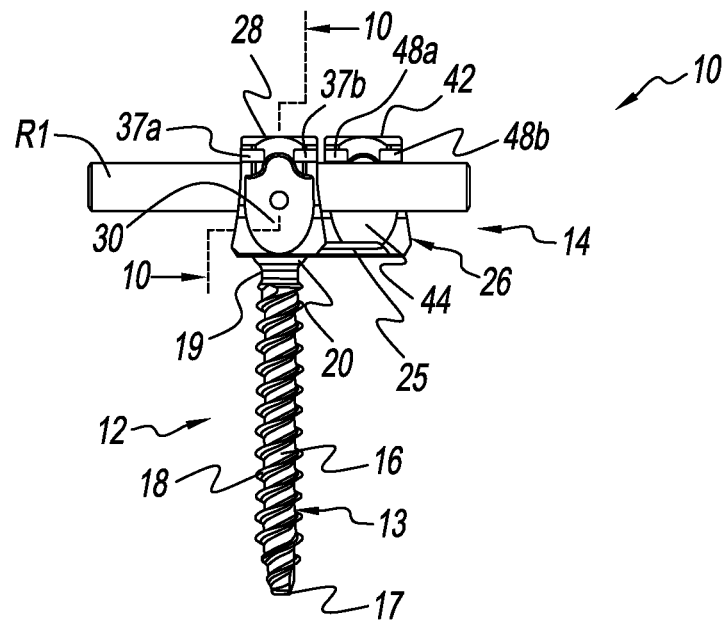
FIG. 9 is a side view of the polyaxial spine screw rod holder having a second, offset spine rod holder of FIG. 4 showing a spine rod retained in the polyaxial spine screw rod holder thereof.
Figure 10:
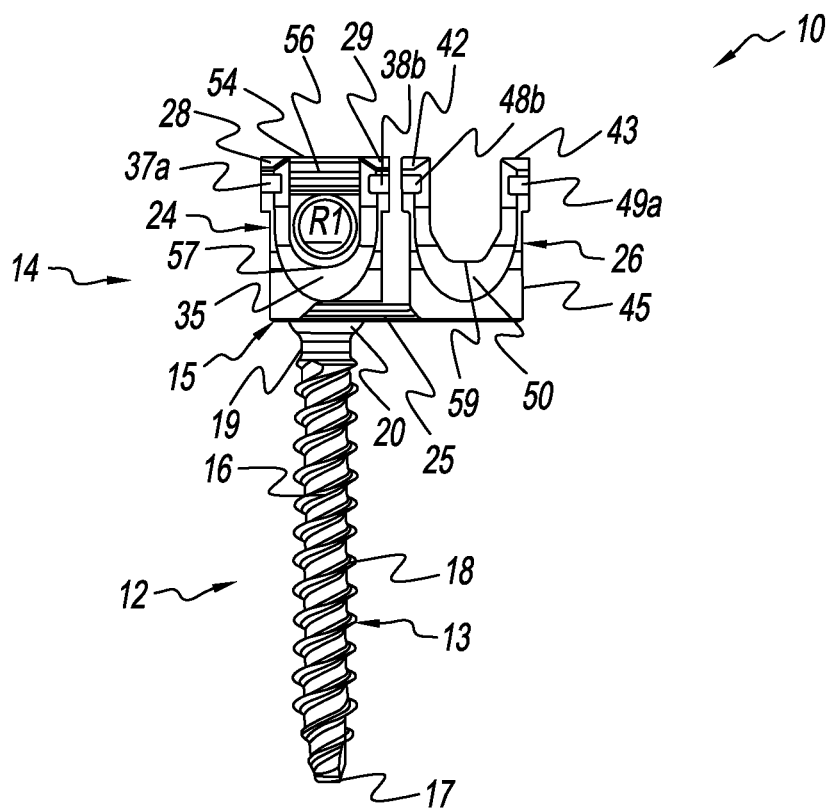
FIG. 10 is a side view of the polyaxial spine screw rod holder having a second, offset spine rod holder of FIG. 4.
Figure 11:
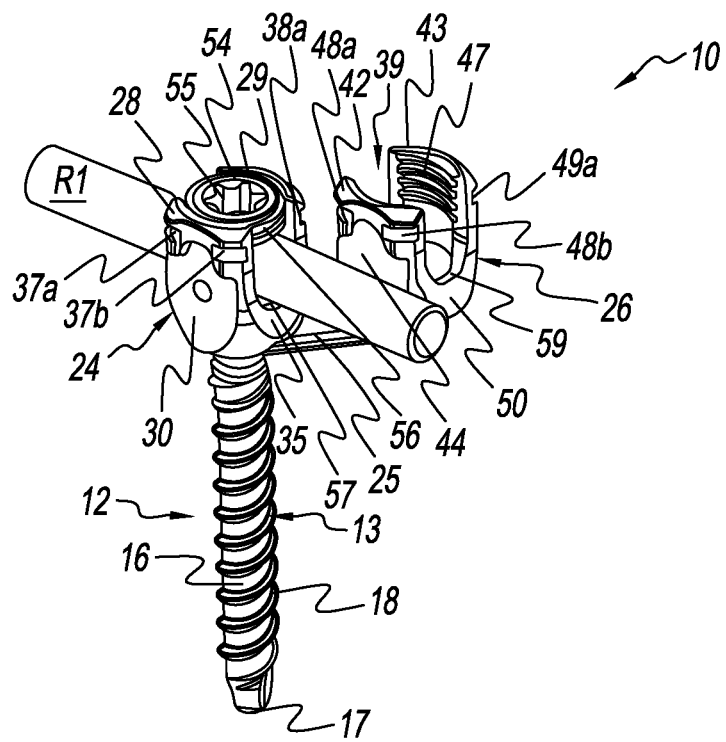
FIG. 11 is a view of the polyaxial spine screw rod holder having a second, offset spine rod holder of FIG. 4 showing a spine rod retained in the polyaxial spine screw rod holder thereof.

FIGS. 4-11 depict several views of a static form of a spine fixation implant embodied as a polyaxial spine screw rod holder assembly 10 comprising a bone screw 12 and a spine rod bone screw holder assembly 14 having a polyaxial spine screw spine rod holder 24, a connector 25, and an offset second rod holder (offset rod holder or second rod holder) 26 fashioned in accordance with the principles of the present invention. The bone screw 12 is adjustably received in the polyaxial spine screw rod holder 24 and extends generally axially downwardly from the bottom of the polyaxial spine screw rod holder 24. The connector 25 is fixed to the polyaxial spine screw rod holder 24 and extends generally radially outwardly from a side of the polyaxial spine screw rod holder 24. The offset second rod holder 26 is fixed to the connector 25 a distance from the polyaxial spine screw rod holder 24. Orientation and/or position of the offset second rod holder 26 is thus static relative to the polyaxial spine screw rod holder 24. All components are made from an implant-suitable, bio-compatible material.

The bone screw 12 is characterized by a body 13 defining a generally elongated shank 16 having a tip 17 and one end of the elongate shank 16 and a head 20 on another end of the elongated shank 16 opposite the tip 17. The head 20 is generally rounded and sized for polyaxial movement in and relative to the polyaxial spine screw rod holder 24 and connects to the elongate shank 16 via a tapered neck 19. A socket 21 is disposed in the top of the head 20 and is configured to receive a like-configured bone screw driver or tool (not shown) for installing the bone screw 12 into vertebral bone (not shown). Threads/threading 18 are disposed on the outside surface of the elongate shank 16 and extend generally between the tip 17 and the neck 19.

The polyaxial spine screw rod holder 24 is generally tulip-shaped having a cavity 34 to allow for receipt of the bone screw 12 and a spine rod (see spine rod R1 of FIGS. 8-11) of any length. The tulip shape of the polyaxial spine screw rod holder 24 defines a first curved wall or side 28 and a second curved wall or side 29, the first and second curved walls 28, 29 opposite one another. The first curved wall 28 has a first flat 30 on its outside surface and threads/threading 32 on its upper inside surface. The first curved wall 28 further has a first notch 37a in a first upper side of its outside surface above the first flat 30, and a second notch 37b in a second upper side of its outside surface above the first flat 30. The first and second notches 37a, 37b allow for reception of a tool (not shown) to install, implant and/or situate the polyaxial spine screw rod holder 24, and/or for other purposes. The second curved wall 29 has a second flat 31 on its outside surface and threads/threading 33 on its upper inside surface. The second curved wall 29 further has a first notch 38a in a first upper side of its outside surface above the second flat 31, and a second notch 38b in a second upper side of its outside surface above the second flat 31. The first and second notches 38a, 38b allow for reception of a tool (not shown) to install, implant and/or situate the polyaxial spine screw rod holder 24, and/or for other purposes.

The tulip shape of the polyaxial spine screw rod holder 24 has a first face 35 between the end side of the first curved wall 28 adjacent the second notch 37b thereof and the end side of the second curved wall 29 adjacent the first notch 38a thereof. A first trough forming a first pocket 57 is defined at the bottom of the first trough, the first pocket 57 configured to receive a section or portion of a spine rod (e.g. spine rod R1 of FIGS. 8-11). The tulip shape of the polyaxial spine screw rod holder 24 further has a second face 35 between the end side of the first curved wall 28 adjacent the first notch 37a thereof and the end side of the second curved wall 29 adjacent the second notch 38b thereof. A second trough forming a second pocket 58 is defined at the bottom of the second trough, the second pocket 58 configured to receive a section of portion of the spine rod (e.g. spine rod R1 of FIGS. 8-11). The first and second pockets 57, 58 together define a first rod seat that holds the spine rod (e.g. the spine rod R1 of FIGS. 8-11). Variations are contemplated.

A set screw 54 is used to fix a spine rod into the polyaxial spine screw rod holder 24. The set screw 54 compresses the spine rod into the first rod seat formed by the first and second pockets 57, 58 which then compresses against the head 20 of the bone screw 12 to lock orientation of the bone screw 12 relative to the polyaxial spine screw rod holder 24 as is known in the art. The set screw 54 is generally cylindrical having circumferential threads/threading on its exterior that are configured to engage the threads/threading 32 and 33 of the first and second curved walls 28, 29. The set screw 54 further has a socket 55 in its upper surface that is configured to receive a like configured driver tool (not shown) for threading the set screw 54 into the polyaxial spine screw rod holder 24.

The connector 25 may take various forms, but is shown as a generally flat body 15 that is fixed to and extends radially outwardly and at an offset (angle) from a side of the polyaxial spine screw rod holder 24. While shown as extending from or proximate to the bottom of the polyaxial spine screw rod holder 24, the connector 25 may extend from other places from the polyaxial spine screw rod holder 24 while maintaining its offset therefrom. The offset is an angle from a side of the polyaxial spine screw rod holder 24. A first rod holder axis is defined as extending through the nadirs of the first and second pockets 57, 58 of the polyaxial spine screw rod holder 24. The first rod holder axis defines a line extending through 0° and 180°. Using the first rod holder axis as the calibration, the offset is preferably, but not necessarily, either forty-five degrees (45°) or one-hundred and thirty-five degrees (135°), however other offsets/angles may be used. According to another definition, the offset is between a perpendicular to the first rod holder axis and a parallel to the first rod holder axis, the offset preferably, but not necessarily, either forty-five degrees (45°) or one-hundred and thirty-five degrees (135°), however other offsets/angles may be used. The first longitudinal axis of the spine rod retained in the polyaxial spine screw rod holder 24 may also be used as the axial calibration.

The offset second rod holder 26 is generally tulip-shaped having a cavity 39 to allow for receipt of a spine rod of any length. The tulip shape of the offset second rod holder 26 defines a first curved wall or side 42 and a second curved wall or side 43, the first and second curved walls 42, 43 opposite one another. The first curved wall 42 has a first flat 44 on its outside surface and threads/threading 46 on its upper inside surface. The first curved wall 42 further has a first notch 48a in a first upper side of its outside surface above the first flat 44, and a second notch 48b in a second upper side of its outside surface above the first flat 44. The first and second notches 48a, 48b allow for reception of a tool (not shown) to install, implant and/or situate the offset second rod holder 26, and/or for other purposes. The second curved wall 43 has a second flat 45 on its outside surface and threads/threading 47 on its upper inside surface. The second curved wall 43 further has a first notch 49a in a first upper side of its outside surface above the second flat 45, and a second notch 49b in a second upper side of its outside surface above the second flat 45. The first and second notches 49a, 49b allow for reception of a tool (not shown) to install, implant and/or situate the offset second rod holder 26, and/or for other purposes.

The tulip shape of the offset second rod holder 26 has a first face 50 between the end side of the first curved wall 42 adjacent the second notch 48b thereof and the end side of the second curved wall 43 adjacent the first notch 49a thereof. A third trough forming a third pocket 59 is defined at the bottom of the third trough, the third pocket 59 configured to receive a section or portion of a spine rod. The tulip shape of the offset second rod holder 26 further has a second face 51 between the end side of the first curved wall 42 adjacent the first notch 48a thereof and the end side of the second curved wall 43 adjacent the second notch 49b thereof. A fourth trough forming a second pocket 60 is defined at the bottom of the fourth trough, the fourth pocket 60 configured to receive a section of portion of a spine rod. The third and fourth pockets 59, 60 together define a second rod seat that holds a spine rod. Variations are contemplated. A second rod holder axis is defined as extending through the nadirs of the third and fourth pockets 59, 60 of the second rod holder 24. The second rod holder axis defines a line extending through 0° and 180°.

The offset second rod holder 26 is fixed to the connector 25 such that its position and orientation is fixed (static) relative to the connector 25. Since the connector 25 is fixed to the polyaxial spine screw rod holder 24, the offset second rod holder 26 is thereby fixed in position and orientation relative to the polyaxial spine screw rod holder 24.

Figure 1:
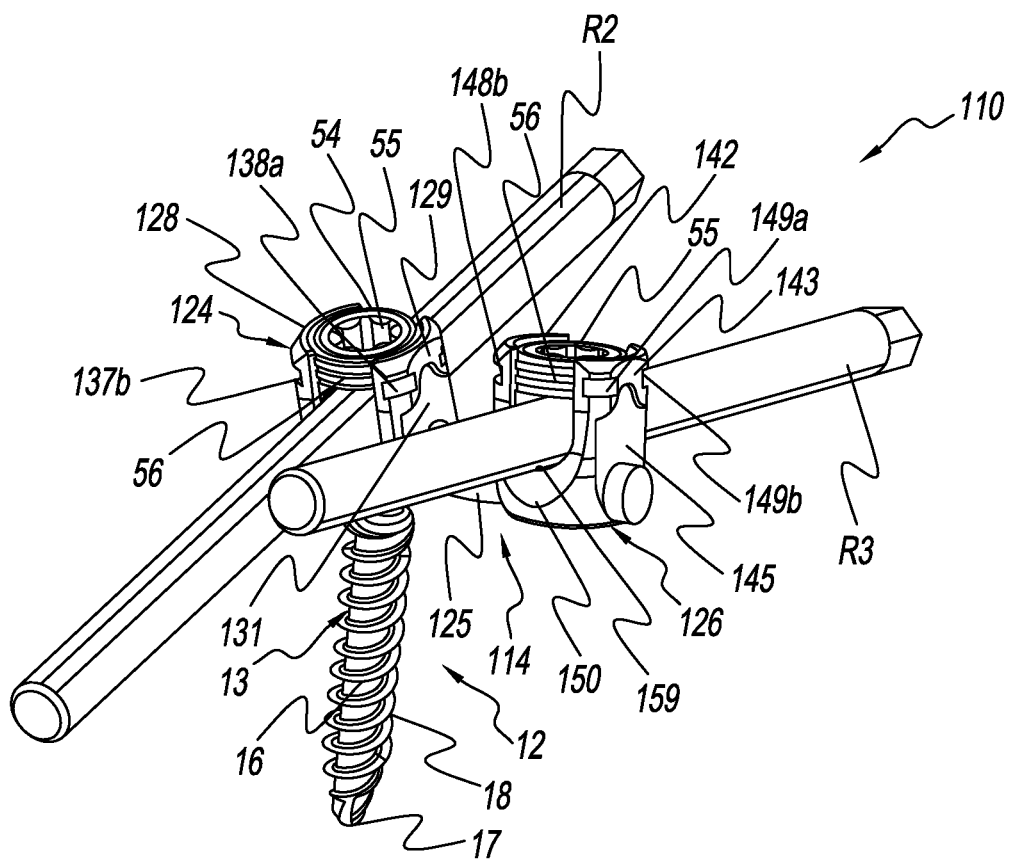
FIG. 1 is a view of one form of a polyaxial spine screw rod holder having a second, offset spine rod holder, showing a spine rod retained in each spine rod holder.
Figure 2:
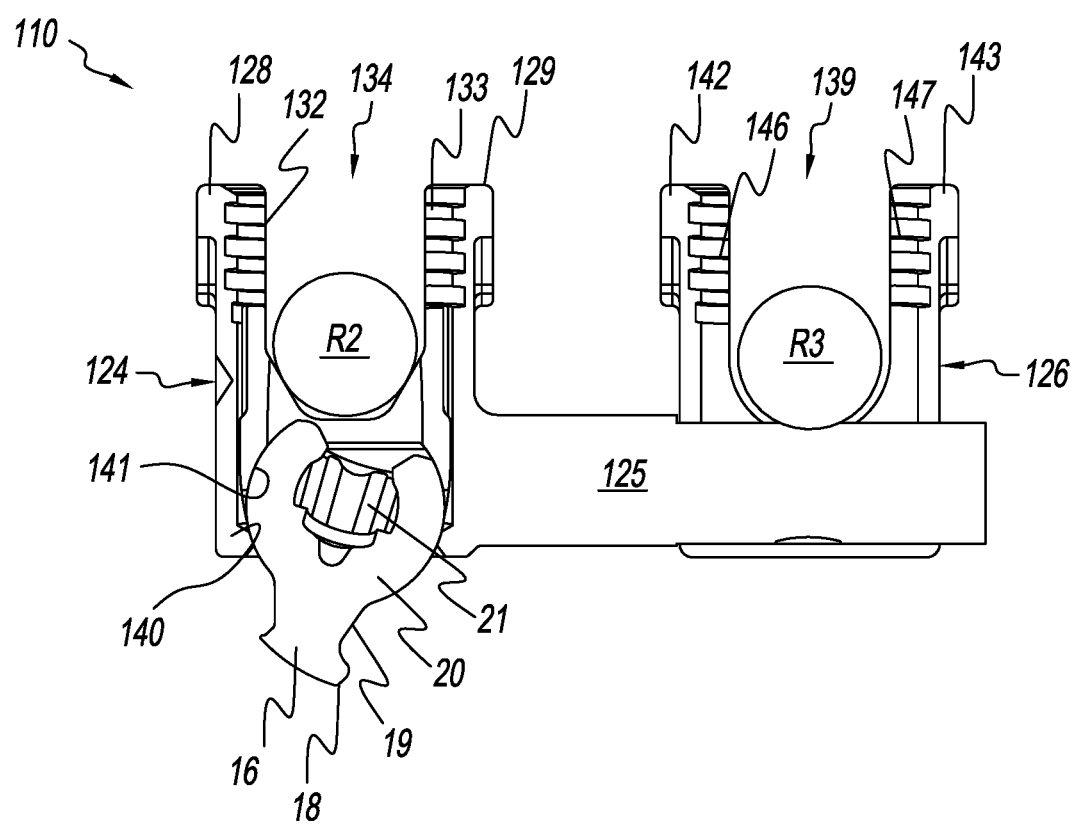
FIG. 2 is a side sectional view of the polyaxial spine screw rod holder having a second, offset spine rod holder of FIG. 1.
Figure 3:
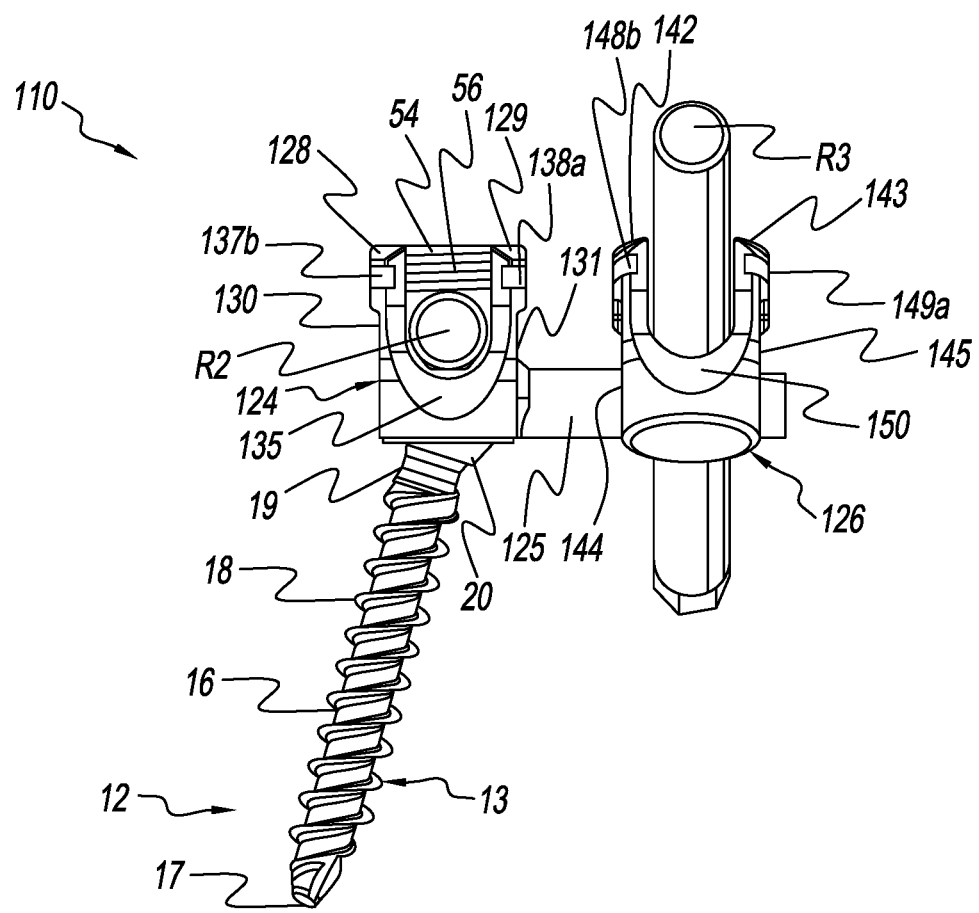
FIG. 3 is another view of the polyaxial spine screw rod holder having a second, offset spine rod holder of FIG. 1 showing a spine rod retained in each spine rod holder.
Figure 12:
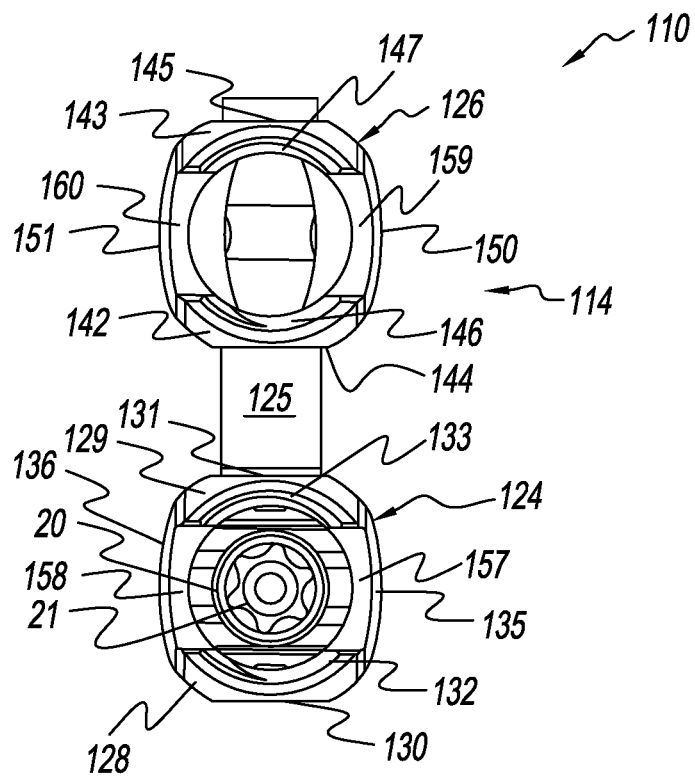
FIG. 12 is an enlarged top plan view of the polyaxial spine screw rod holder having a second, offset spine rod holder of FIG. 1.
Figure 13:
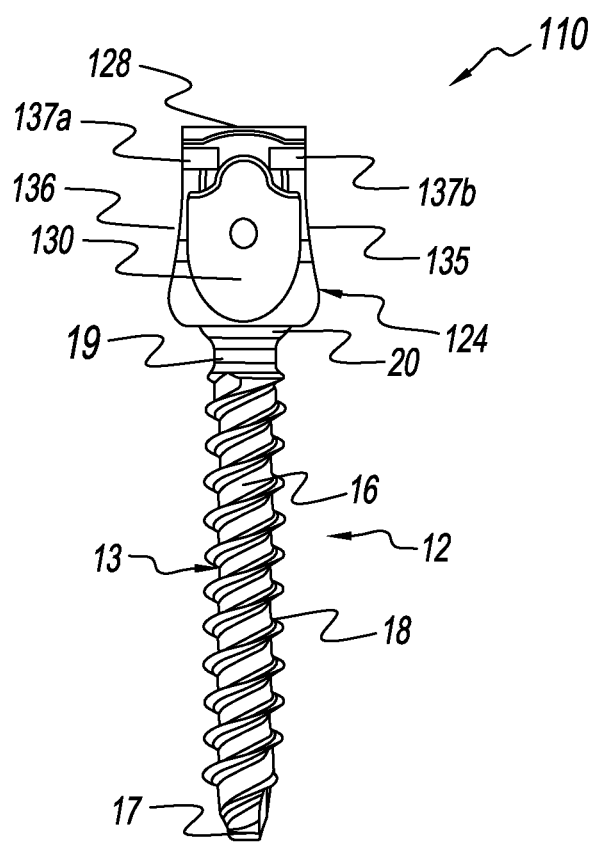
FIG. 13 is a side view of the polyaxial spine screw rod holder having a second, offset spine rod holder of FIG. 1.
Figure 14:
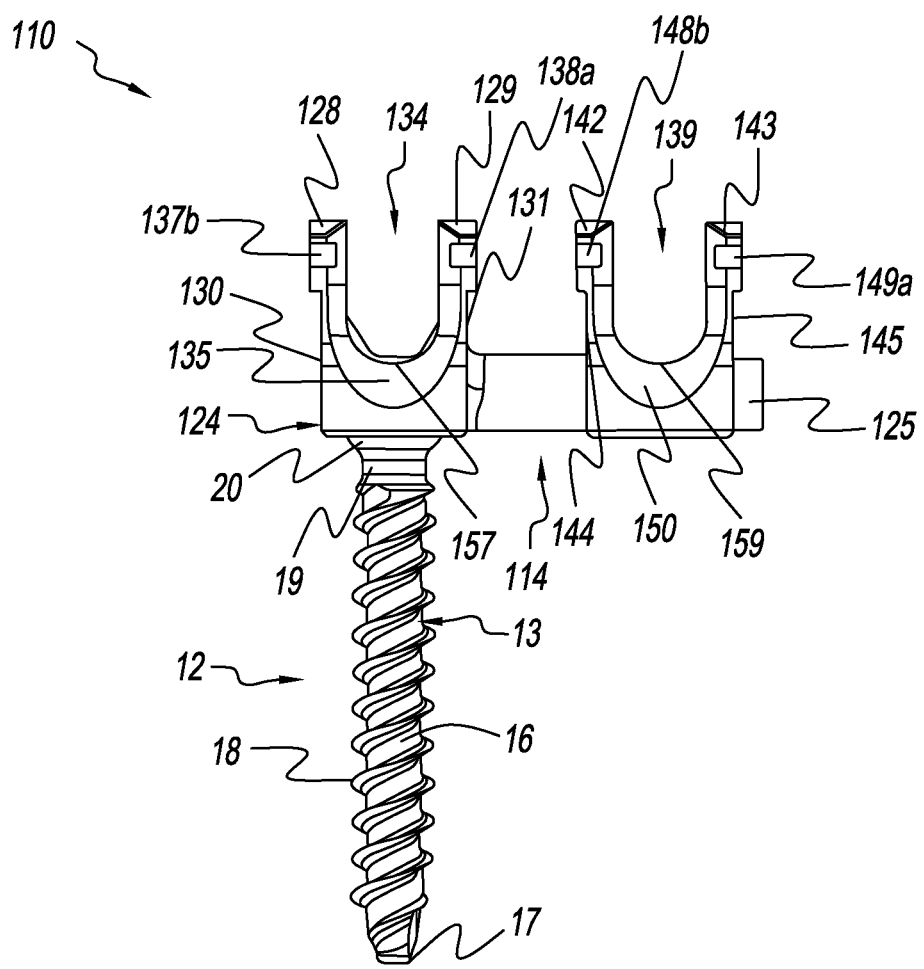
FIG. 14 is another side view of the polyaxial spine screw rod holder having a second, offset spine rod holder of FIG. 1.
Figures 15, 16:
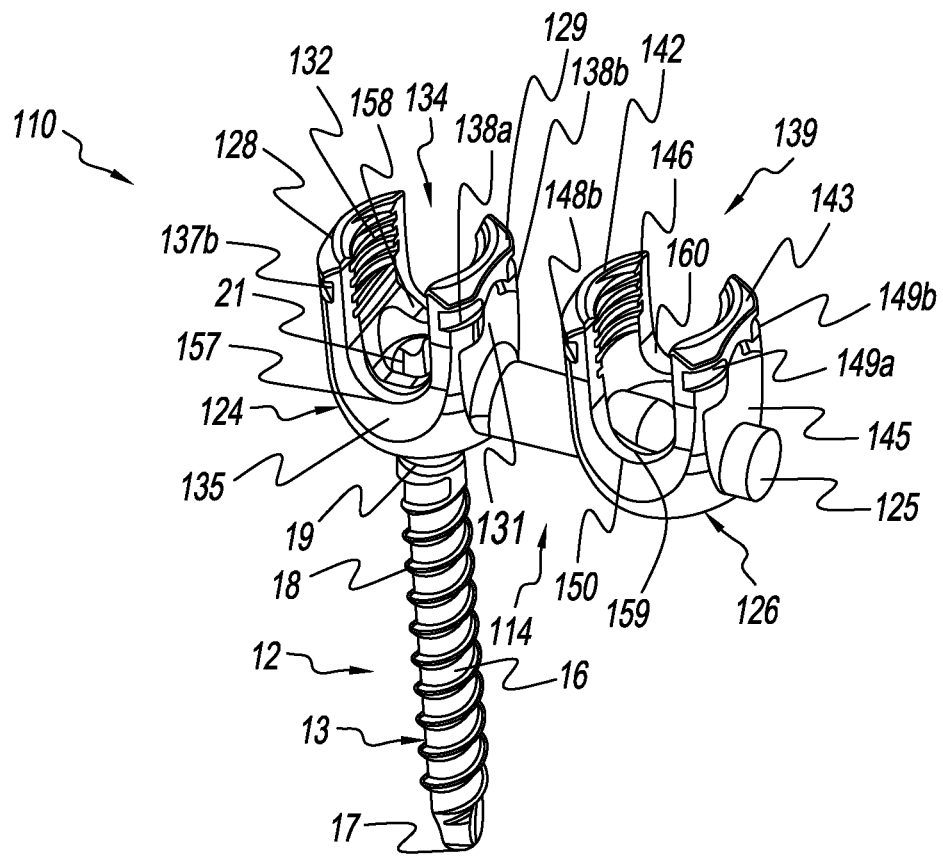
FIG. 15 is a view of the polyaxial spine screw rod holder having a second, offset spine rod holder of FIG. 1.
FIG. 16 is a top plan view of the polyaxial spine screw rod holder having a second, offset spine rod holder of FIG. 1 showing a spine rod in each spine rod holder thereof.
Figure 17:
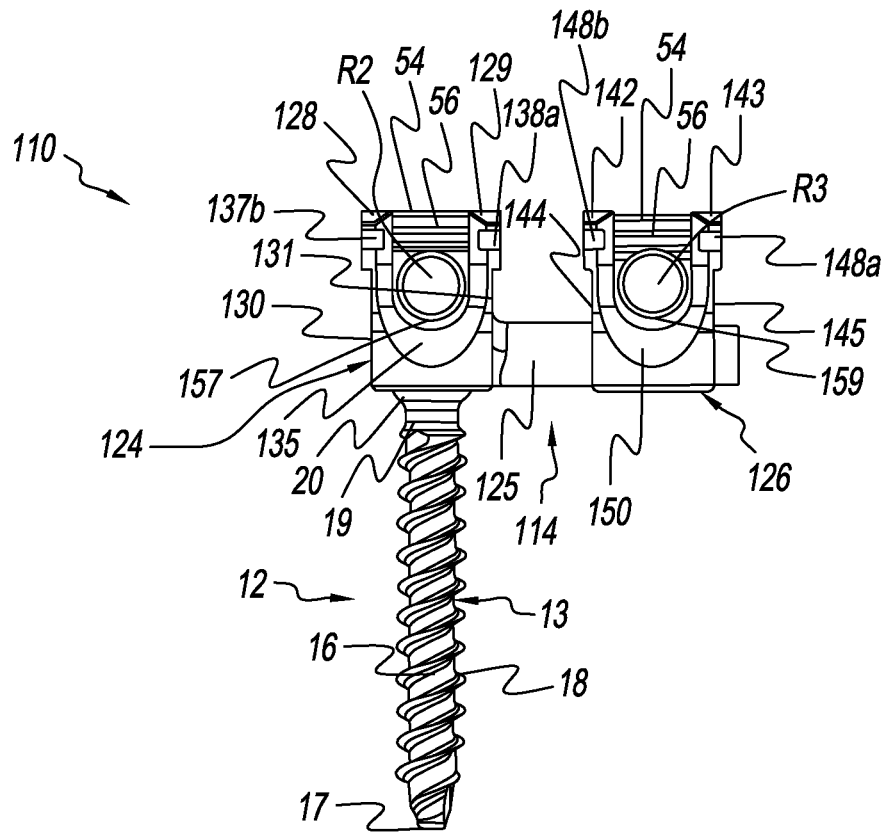
FIG. 17 is a side view of the polyaxial spine screw rod holder having a second, offset spine rod holder of FIG. 1 showing a spine rod in each spine rod holder thereof.
Figure 18:
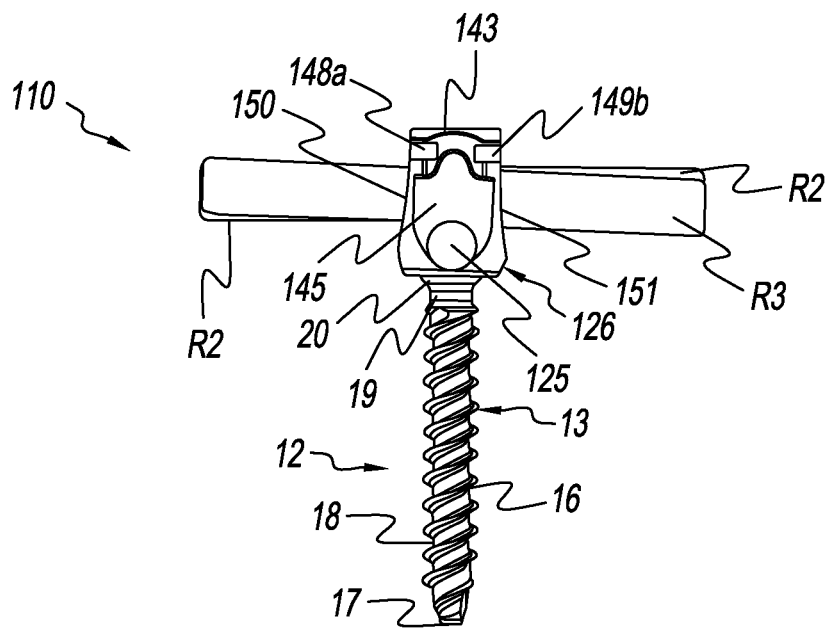
FIG. 18 is another side view of the polyaxial spine screw rod holder having a second, offset spine rod holder of FIG. 1 showing a spine rod in each spine rod holder thereof.

FIGS. 1-3 and 12-18 depict several views of a dynamic form of a spine fixation implant embodied as a polyaxial spine screw rod bone screw assembly 110 comprising a bone screw 12 and a spine rod holder assembly 114 having a polyaxial spine screw spine rod holder 124, a connector 125, and an offset second rod holder 126 fashioned in accordance with the principles of the present invention. The bone screw 12 is adjustably received in the polyaxial spine screw rod holder 124 and extends generally axially downwardly from the bottom of the polyaxial spine screw rod holder 124. The connector 125 is preferably, but not necessarily, part of the polyaxial spine screw rod holder 124. Regardless, the connector 125 is fixed to the polyaxial spine screw rod holder 124. The connector 125 extends generally radially outwardly from a side of the polyaxial spine screw rod holder 124. The offset second rod holder 126 is movably mounted on the connector 125. Orientation and position of the offset second rod holder 126 is thus dynamic relative to the polyaxial spine screw rod holder 124. The offset second rod holder 126 is movable on the connector 125 such that distance from (or between) the offset second rod holder 126 is adjustably variable relative to the polyaxial spine screw rod holder 124. The offset second rod holder 126 is also rotatable on and relative to the connector 125. This allows rotational variable adjustment (orientation) of the offset second rod holder 126 relative to the polyaxial spine screw rod holder 124. All components are made from an implant-suitable, bio-compatible material.

The bone screw 12 is the same as described above and so will not be described again.

The polyaxial spine screw rod holder 124 is generally tulip-shaped having a cavity 134 to allow for receipt of the bone screw 12 and a spine rod R2 (see FIGS. 1-3 and 16-18) of any length. The tulip shape of the polyaxial spine screw rod holder 124 defines a first curved wall or side 128 and a second curved wall or side 129, the first and second curved walls 128, 129 opposite one another. The first curved wall 128 has a first flat 130 on its outside surface and threads/threading 132 on its upper inside surface. The first curved wall 128 further has a first notch 137a in a first upper side of its outside surface above the first flat 130, and a second notch 137b in a second upper side of its outside surface above the first flat 130. The first and second notches 137a, 137b allow for reception of a tool (not shown) to install, implant and/or situate the polyaxial spine screw rod holder 124, and/or for other purposes. The second curved wall 129 has a second flat 131 on its outside surface and threads/threading 133 on its upper inside surface. The second curved wall 129 further has a first notch 138a in a first upper side of its outside surface above the second flat 131, and a second notch 138b in a second upper side of its outside surface above the second flat 131. The first and second notches 138a, 138b allow for reception of a tool (not shown) to install, implant and/or situate the polyaxial spine screw rod holder 124, and/or for other purposes.

The tulip shape of the polyaxial spine screw rod holder 124 has a first face 135 between the end side of the first curved wall 128 adjacent the second notch 137b thereof and the end side of the second curved wall 129 adjacent the first notch 138a thereof. A first trough forming a first pocket 157 is defined at the bottom of the first trough, the first pocket 157 configured to receive a section or portion of a spine rod R2 (see FIGS. 1-3 and 16-18). The tulip shape of the polyaxial spine screw rod holder 124 further has a second face 135 between the end side of the first curved wall 128 adjacent the first notch 137a thereof and the end side of the second curved wall 129 adjacent the second notch 138b thereof. A second trough forming a second pocket 158 is defined at the bottom of the second trough, the second pocket 158 configured to receive a section of portion of the spine rod R2. The first and second pockets 157, 158 together define a first rod seat that holds the spine rod R2. Variations are contemplated.

A set screw 54 is used to fix the spine rod R2 into the polyaxial spine screw rod holder 124. The set screw 54 compresses the spine rod R2 into the first rod seat formed by the first and second pockets 157, 158 which then compresses against the head 20 of the bone screw 12 to lock orientation of the bone screw 12 relative to the polyaxial spine screw rod holder 124 as is known in the art. The set screw 54 is configured as described above such that its exterior threads/threading engage the threads/threading 132 and 133 of the first and second curved walls 128, 129.

The connector 125 may take various forms, but is shown as an elongated cylindrical dowel, bar, rod, or the like 125 that is fixed to and extends radially outwardly and at an offset (angle) from a side of the polyaxial spine screw rod holder 124. While shown as extending from or proximate to the bottom of the polyaxial spine screw rod holder 124, the connector 125 may extend from other places from the polyaxial spine screw rod holder 124 while maintaining its offset therefrom. The offset is an angle from a side of the polyaxial spine screw rod holder 124. A first rod holder axis is defined as extending through the nadirs of the first and second pockets 157, 158 of the polyaxial spine screw rod holder 124. The first rod holder axis defines a line extending through 0° and 180°. Using the first rod holder axis as the calibration, the offset is preferably, but not necessarily, ninety degrees (90°), however other offsets/angles may be used. According to another definition, the offset is a perpendicular to the first rod holder axis, however other offsets/angles may be used. The first longitudinal axis of the spine rod R2 retained in the polyaxial spine screw rod holder 124 may also be used as the axial calibration.

The offset second rod holder 126 is generally tulip-shaped having a cavity 139 to allow for receipt of the spine rod R3 (see e.g., FIGS. 1-3, 16-18) of any length. The tulip shape of the offset second rod holder 126 defines a first curved wall or side 142 and a second curved wall or side 143, the first and second curved walls 142, 143 opposite one another. The first curved wall 142 has a first flat 144 on its outside surface and threads/threading 146 on its upper inside surface. The first curved wall 142 further has a first notch 148a in a first upper side of its outside surface above the first flat 144, and a second notch 148b in a second upper side of its outside surface above the first flat 144. The first and second notches 148a, 148b allow for reception of a tool (not shown) to install, implant and/or situate the offset second rod holder 126, and/or for other purposes. The second curved wall 143 has a second flat 145 on its outside surface and threads/threading 147 on its upper inside surface. The second curved wall 143 further has a first notch 149a in a first upper side of its outside surface above the second flat 145, and a second notch 149b in a second upper side of its outside surface above the second flat 145. The first and second notches 149a, 149b allow for reception of a tool (not shown) to install, implant and/or situate the offset second rod holder 126, and/or for other purposes.

The tulip shape of the offset second rod holder 126 has a first face 150 between the end side of the first curved wall 142 adjacent the second notch 148b thereof and the end side of the second curved wall 143 adjacent the first notch 149a thereof. A third trough forming a third pocket 59 is defined at the bottom of the third trough, the third pocket 159 configured to receive a section or portion of a spine rod (e.g. spine rod R3). The tulip shape of the offset second rod holder 126 further has a second face 151 between the end side of the first curved wall 142 adjacent the first notch 148a thereof and the end side of the second curved wall 143 adjacent the second notch 149b thereof. A fourth trough forming a second pocket 160 is defined at the bottom of the fourth trough, the fourth pocket 160 configured to receive a section of portion of a spine rod. The third and fourth pockets 159, 160 together define a second rod seat that holds a spine rod. Variations are contemplated. A second rod holder axis is defined as extending through the nadirs of the third and fourth pockets 159, 160 of the second rod holder 124. The second rod holder axis defines a line extending through 0° and 180°.

A set screw 54 is used to fix the spine rod R3 into the offset second rod holder 126. The set screw 54 compresses the spine rod R3 into the second rod seat formed by the third and fourth pockets 159, 160 to lock orientation of the spine rod R3 relative to the offset second rod holder 126. The set screw 54 is configured as described above such that its exterior threads/threading engage the threads/threading 146 and 147 of the first and second curved walls 142, 143.

It should be appreciated that dimensions of the components, structures, and/or features of the present implant may be altered as desired within the scope of the present disclosure.

What is claimed is:

1. A spine fixation implant comprising:
a bone screw having a bone screw head and a bone screw longitudinal axis;
a polyaxial spine screw rod holder disposed on the bone screw head and configured to retain a first spine rod having a first longitudinal axis at a first axial orientation transverse to the bone screw longitudinal axis;
a first set screw receivable in the polyaxial spine screw rod holder that locks axial position of the polyaxial spine screw rod holder on the bone screw head and locks the first spine rod to the polyaxial spine screw rod holder;
a connector formed integral to the polyaxial spine rod holder and extending from a lower side of the polyaxial spine rod holder transverse to the first axial orientation of the first spine rod, the connector having a connector longitudinal axis;
a screw-less spine rod holder situated on the connector for rotation about the connector longitudinal axis and configured to retain a second spine rod having a second longitudinal axis at a second axial orientation; and
a second set screw receivable in the screw-less spine rod holder that locks rotational position of the screw-less spine rod holder on the connector and locks the second spine rod to the screw-less spine rod holder.

2. The spine fixation implant of claim 1, wherein rotational position of the screw-less spine rod holder is variably adjustable relative to the connector.

3. The spine fixation implant of claim 2, wherein the screw-less spine rod holder is spatially variably adjustable on the connector relative to the polyaxial spine screw rod holder.

4. The spine fixation implant of claim 3, wherein the polyaxial spine screw rod holder has a first rod seat configured to receive the first spine rod, and the screw-less spine rod holder has a second rod seat configured to receive the second spine rod.

5. The spine fixation implant of claim 4, wherein orientation of the second rod seat of the screw-less spine rod holder is rotatable relative to the orientation of the first rod seat of the polyaxial spine screw rod holder such that the second longitudinal axis of the second spine rod retained in the second rod seat of the screw-less spine rod holder is rotationally positionable relative to the first longitudinal axis of the first spine rod retained in the first rod seat of the polyaxial spine screw rod holder, and spatial orientation of the second rod seat of the screw-less spine rod holder is independently positionable relative to the first rod seat of the polyaxial spine screw rod holder such that distance between the second spine rod retained in the second rod seat of the screw-less spine rod holder relative to the first spine rod retained in the first rod seat of the polyaxial spine screw rod holder is adjustable.

6. The spine fixation implant of claim 4, wherein the first rod seat of the polyaxial spine screw rod holder is defined by first and second rod pockets, and the second rod seat of the screw-less spine rod holder is defined by third and fourth rod pockets.

7. The spine fixation implant of claim 3, wherein the offset is a perpendicular to the first longitudinal axis of the first spine rod retained in the polyaxial spine screw rod holder.

8. The spine fixation implant of claim 7, wherein the offset is ninety degrees) (90° from the perpendicular to the first longitudinal axis of the first spine rod retained in the polyaxial spine screw rod holder.

9. A method of spine fixation comprising:
providing a spine implant having a bone screw with a bone screw head and a bone screw longitudinal axis, a polyaxial spine screw rod holder disposed on the bone screw head and configured to retain a first spine rod having a first longitudinal axis at a first axial orientation transverse to the bone screw longitudinal axis, a first set screw receivable in the polyaxial spine screw rod holder that locks axial position of the polyaxial spine screw rod holder on the bone screw head and locks the first spine rod to the polyaxial spine screw rod holder, a connector formed integral to the polyaxial spine rod holder and extending from a lower side of the polyaxial spine rod holder transverse to the first axial orientation of the first spine rod, the connector having a connector longitudinal axis, a screw-less spine rod holder situated on the connector for rotation about the connector longitudinal axis and configured to retain a second spine rod having a second longitudinal axis at a second axial orientation; and a second set screw receivable in the screw-less spine rod holder that locks rotational position of the screw-less spine rod holder on the connector and locks the second spine rod to the screw-less spine rod holder; and
installing the spine implant on vertebrae of a spine.

10. The method of claim 9, wherein the offset is between a perpendicular to the first longitudinal axis of the first spine rod retained in the polyaxial spine screw rod holder and a parallel to the first longitudinal axis of the first spine rod retained in the polyaxial spine screw rod holder.

* * * * *